(12) United States Patent
Hirai et al.

(10) Patent No.: US 11,382,533 B2
(45) Date of Patent: Jul. 12, 2022

(54) MOTION ANALYZING DEVICE

(71) Applicant: OSAKA UNIVERSITY, Osaka (JP)

(72) Inventors: Hiroaki Hirai, Osaka (JP); Fumiaki Yoshikawa, Osaka (JP); Eichi Watanabe, Osaka (JP); Yuma Nagakawa, Osaka (JP); Akira Kuroiwa, Osaka (JP); Mitsunori Uemura, Osaka (JP); Fumio Miyazaki, Osaka (JP)

(73) Assignee: Osaka University, Osaka (JP)

( * ) Notice: Subject to any disclaimer, the term of this patent is extended or adjusted under 35 U.S.C. 154(b) by 529 days.

(21) Appl. No.: 16/330,409

(22) PCT Filed: Sep. 6, 2017

(86) PCT No.: PCT/JP2017/032049
§ 371 (c)(1),
(2) Date: Mar. 5, 2019

(87) PCT Pub. No.: WO2018/047847
PCT Pub. Date: Mar. 15, 2018

(65) Prior Publication Data
US 2021/0290108 A1 Sep. 23, 2021

(30) Foreign Application Priority Data
Sep. 6, 2016 (JP) .............................. JP2016-173385

(51) Int. Cl.
*A61B 5/11* (2006.01)
*A61B 5/389* (2021.01)
(Continued)

(52) U.S. Cl.
CPC ............ *A61B 5/1126* (2013.01); *A61B 5/107* (2013.01); *A61B 5/389* (2021.01); *A61B 5/6824* (2013.01)

(58) Field of Classification Search
CPC ..... A61B 5/1126; A61B 5/6824; A61B 5/389; A61B 5/107
See application file for complete search history.

(56) References Cited

U.S. PATENT DOCUMENTS 9,034,055 B2  5/2015  Vinjamuri
9,498,623 B2  11/2016 Shimoda
(Continued)

FOREIGN PATENT DOCUMENTS

JP  2015-073805 A  4/2015
JP  2015-112453 A  6/2015
(Continued)

OTHER PUBLICATIONS

Chen K. Modeling of equilibrium point trajectory control in human arm movements. PhD Thesis, New Jersey Institute of Technology, 2011. (Year: 2011).*

(Continued)

*Primary Examiner* — Devin B Henson
*Assistant Examiner* — Justin Xu
(74) *Attorney, Agent, or Firm* — Renner, Otto, Boisselle & Sklar, LLP

(57) ABSTRACT

A motion analyzing device includes a myogenic potential measuring unit (20) and a myogenic potential measurement processor (101) to measure the muscle activity of a person who performs a motion and a motion measuring unit (30) and a position measurement processor (102) to measure the body motion. The motion analyzing device also includes an AA muscle co-activation ratio calculating unit (103), a muscle synergy calculating unit (104) and an equilibrium point calculating unit (105) to calculate an equilibrium point of the person and a muscle synergy that is a set of base vectors describing the equilibrium point based on a musculoskeletal model of the person and a constraint condition that (Continued)

the position of the endpoint of the limb matches the position of the equilibrium point in a static situation to keep a posture still under gravity compensation.

4 Claims, 11 Drawing Sheets

(51) Int. Cl.
 *A61B 5/00* (2006.01)
 *A61B 5/107* (2006.01)

(56) References Cited

U.S. PATENT DOCUMENTS

| 2012/0172745 | A1 | 7/2012 | Miyazaki |
| 2015/0106023 | A1 | 4/2015 | Shimoda |
| 2016/0324436 | A1 | 11/2016 | Miyazaki |

FOREIGN PATENT DOCUMENTS

| WO | 2011/030781 | A | 3/2011 |
| WO | 2015/093224 | A | 6/2015 |

OTHER PUBLICATIONS

International Search Report (ISR) for corresponding App. No. PCT/JP2017/032049, dated Nov. 7, 2017.
International Preliminary Examination Report (IPRP) for corresponding App. No. PCT/JP2017/032049, dated Jul. 24, 2018.
Kanna Uno, "Muscle Synergies, Equilibrium-point Trajectory and Endpoint Stiffness during Human Upper-limb Movements on a Horizontal Plane: an Approach using EMG Signals", Journal of the Robotics Society of Japan, Sep. 15, 2014 (Sep. 15, 2014), vol. 32, No. 7, p. 29 to 40, particularly, p. 30, right column, line 24 to p. 37, right column, line 10. (w/ English Abstract).
H. Hirai, F. Miyazaki, H. Naritomi, K. Koba, T. Oku, K. Uno, M. Uemura, T. Nishi, M. Kageyama and H. I. Krebs, "On the Origin of Muscle Synergies: Invariant Balance in the Co-activation of Agonist and Antagonist Muscle Pairs." Front. Bioeng. Biotechnol., vol. 3, No. 192, pp. 1-16, 2015.
F. Yoshikawa, H. Hirai, E. Watanabe, Y. Nagakawa, A. Kuroiwa, E. P. Grabke, M. Uemura, F. Miyazaki, and H. I. Krebs, "Equilibrium-point-based Synergies that Encode Coordinates in Task Space: A Practical Method for Translating Functional Synergies from Human to Musculoskeletal Robot Arm," Proc IEEE-RAS Int Conf Humanoid Robots (Humanoids2016), pp. 1135-1140, 2016.

* cited by examiner

Schematic of system configuration

F I G . 2
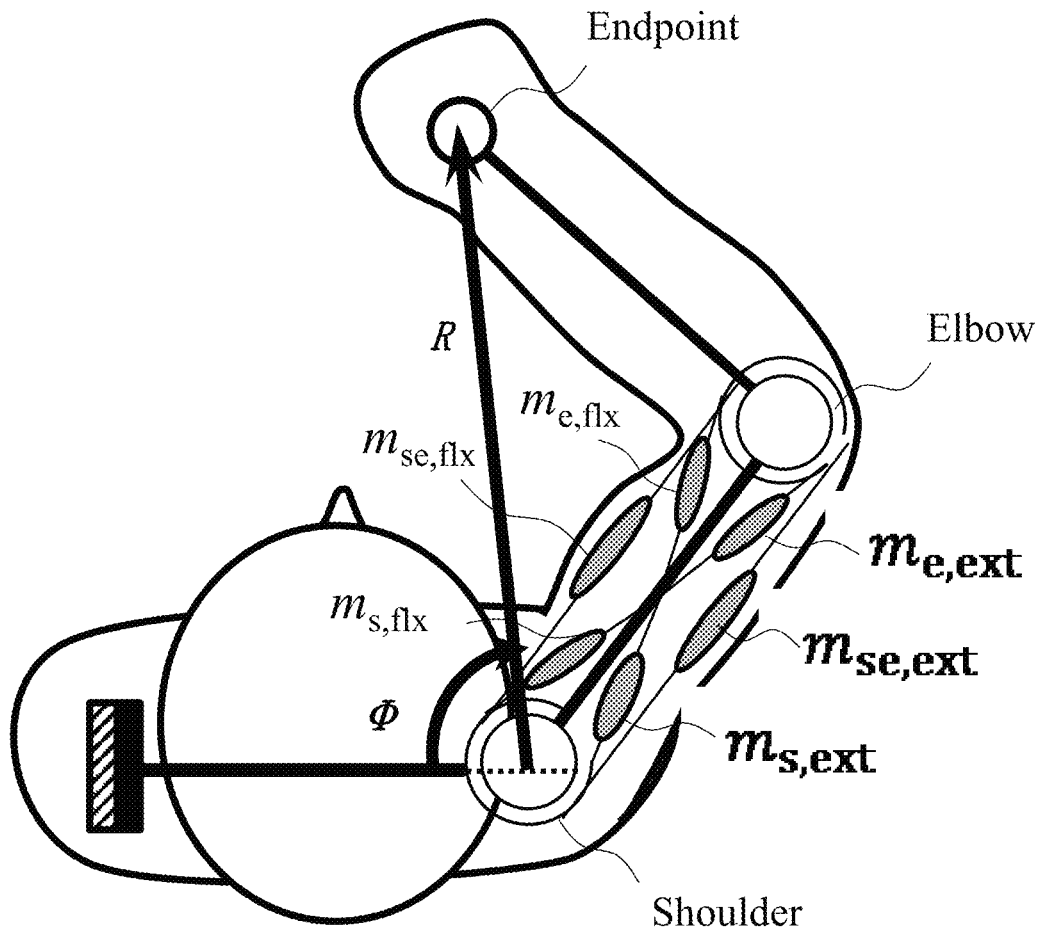
ms,ext : DELTOID POSTERIOR
ms,flx : DELTOID ANTERIOR
mse,ext : LONG HEAD OF TRICEPS BRACHII
mse,flx : BICEPS BRACHII
me,ext : LATERAL HEAD OF TRICEPS BRACHII
me,flx : BRACHIORADIALIS

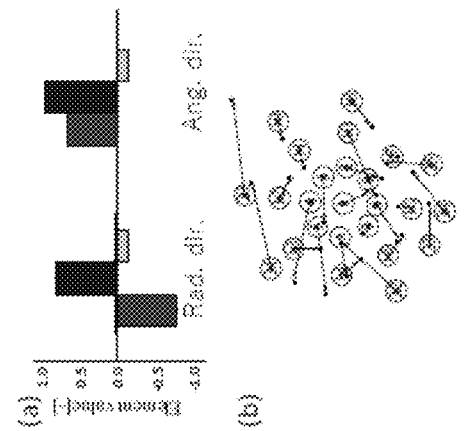
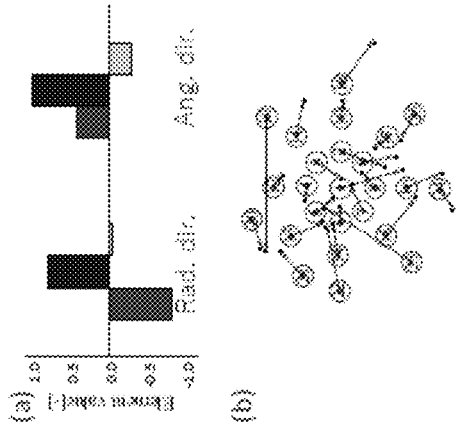
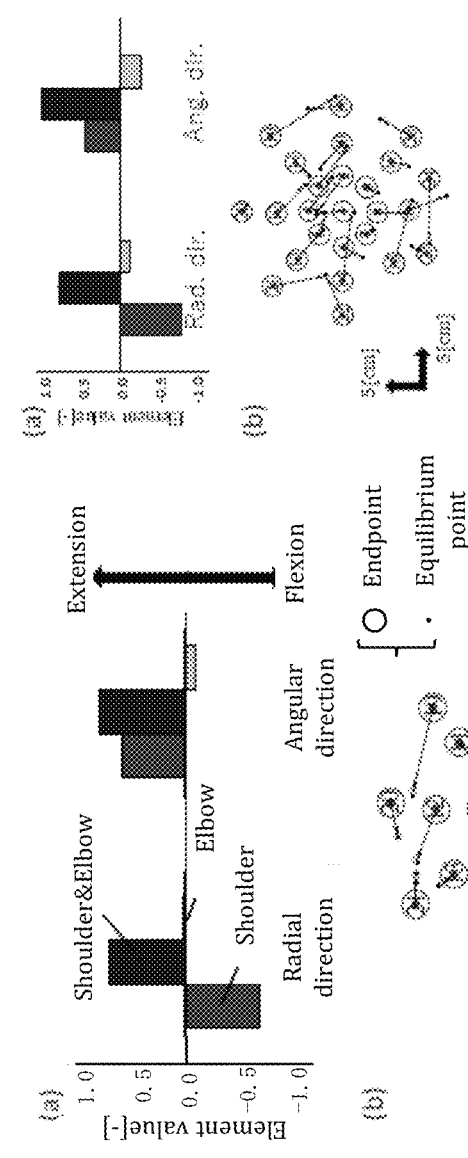
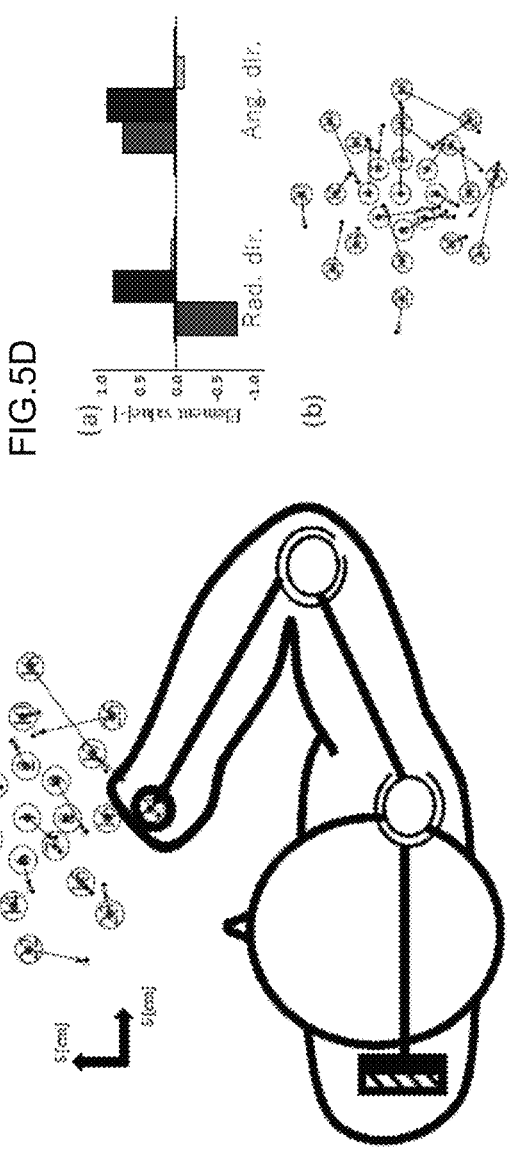
Five subjects' EP-based synergies that encode polar coordinates in task space. (a) Synergy vector, (b) Endpoint EP and endpoint position End point (3, 5, 7, 9)

End point (11, 13, 15, 17)

Variability of endpoint EP at representative endpoint positions: (A) Innermost circle, (B) Middle circle

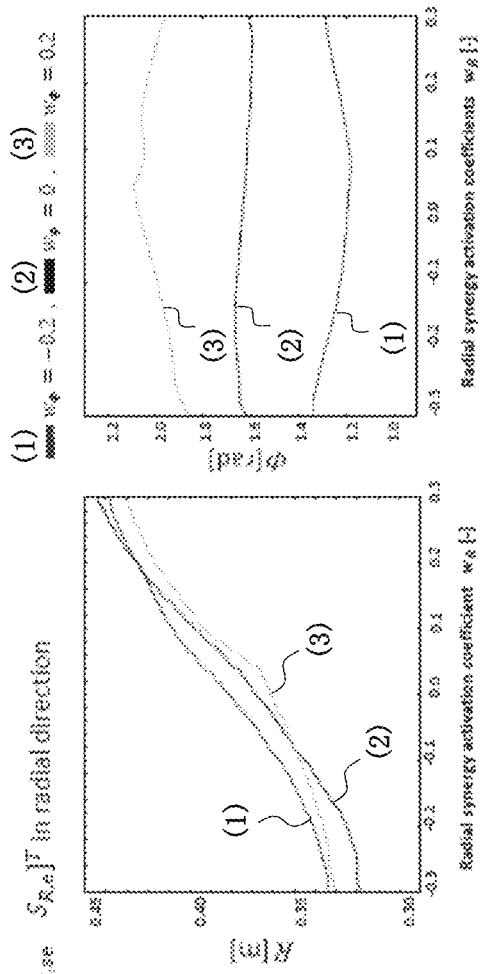
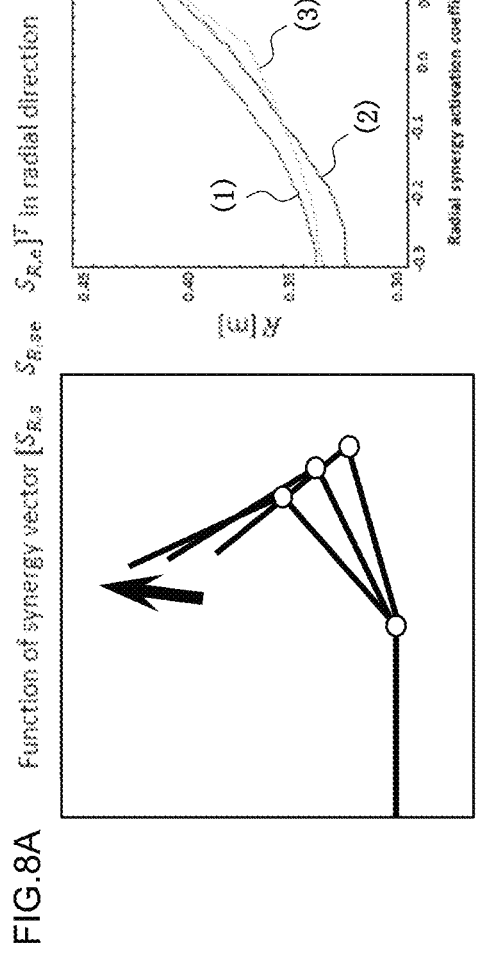
FIG.8A
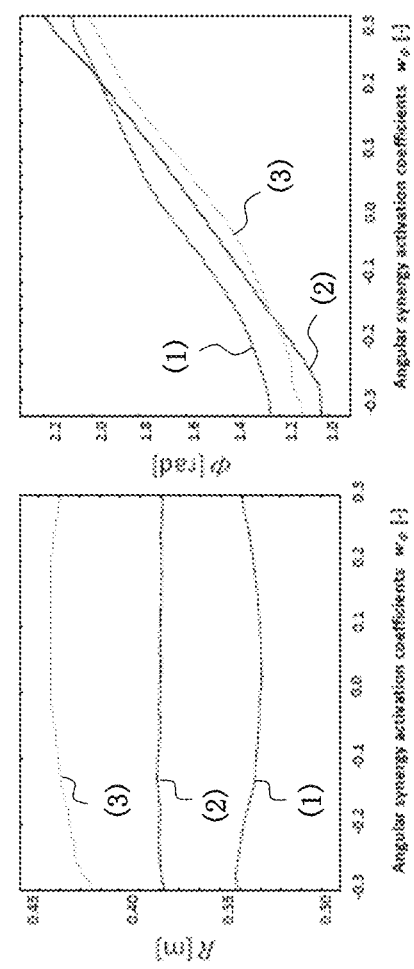
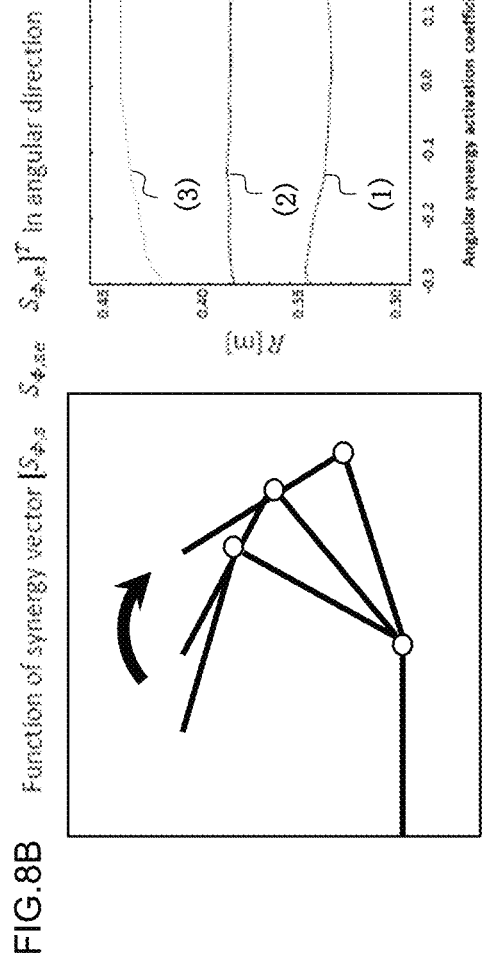
FIG.8B
Physical interpretation of two of the synergy vectors. (A) Function of synergy vector $[S_{R,s}, S_{R,se}, S_{R,e}]^T$ in radial direction. (B) Function of synergy vector $[S_{\phi,s}, S_{\phi,se}, S_{\phi,e}]^T$ in angular direction

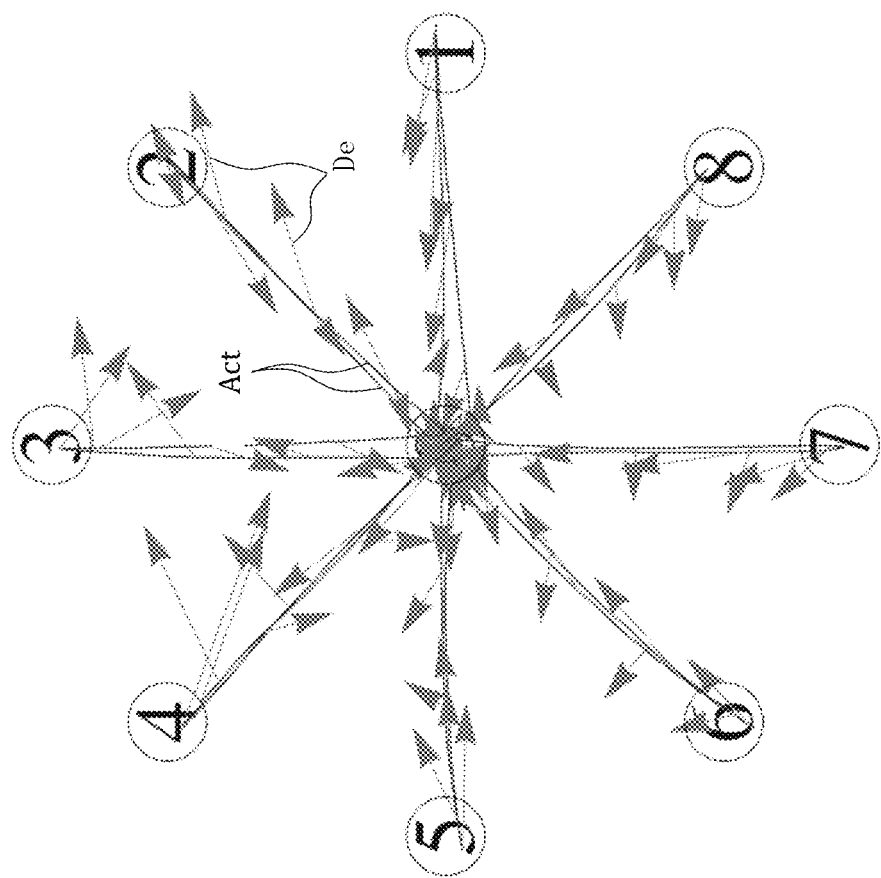

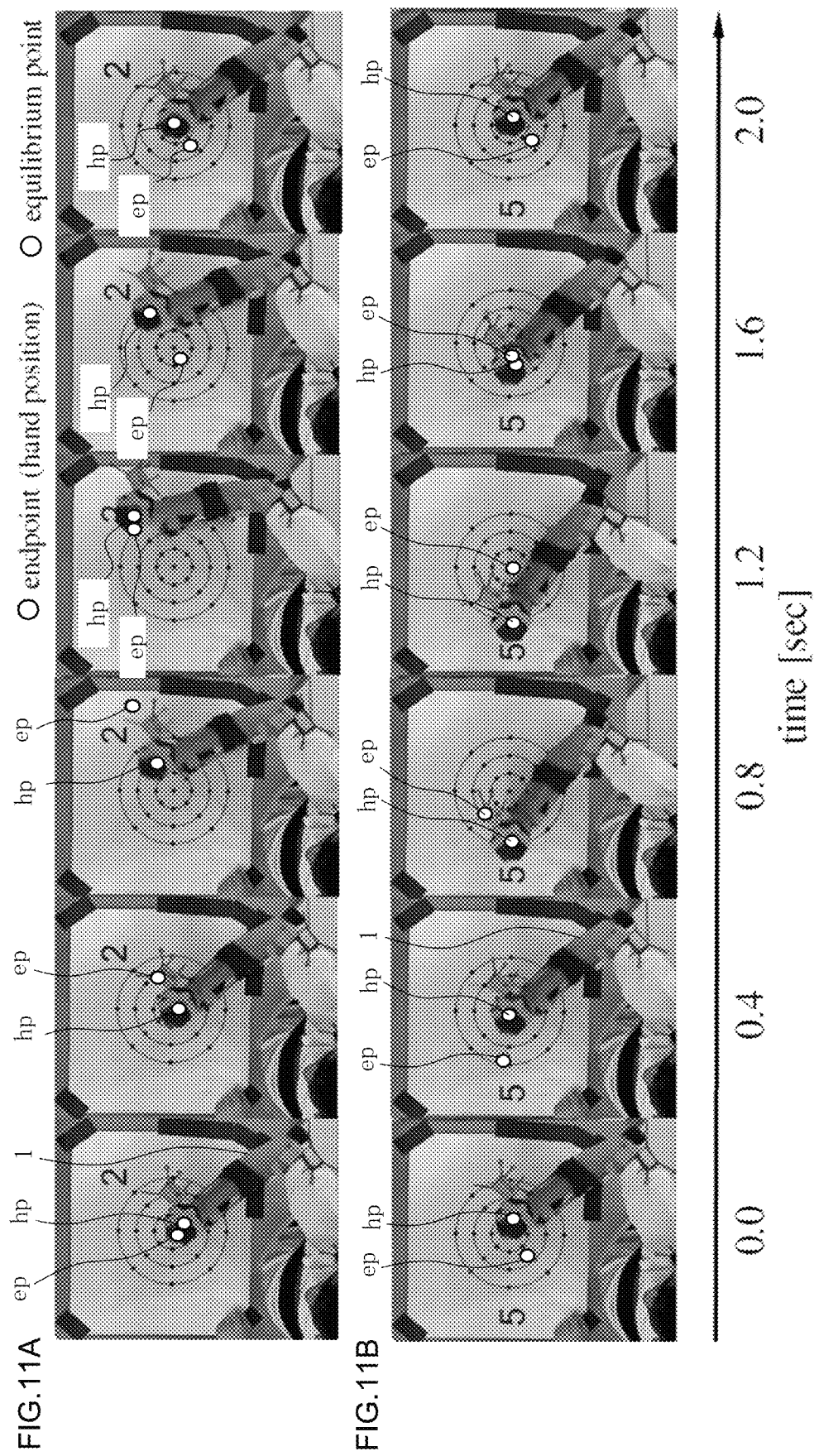

MOTION ANALYZING DEVICE

TECHNICAL FIELD

The present invention relates to a motion analyzing technique of calculating a feature amount relating to the motion control for an operating point at a suitable part of a body, e.g., at an endpoint of a limb.

BACKGROUND ART

As the population ages rapidly, science and technology to assist the human's health promotion draw a lot of expectations. Adequate assistance for health promotion needs the correct theory and the scientific basis supporting the theory. Humans have a body-moving system that is kinematically and dynamically redundant and has multiple degrees of freedom, and the field of analyzing human's motion control has a long-standing unsolved problem about how the central nervous system manipulates the degrees of freedom and determines the muscle activity pattern, and what rules control the motion. The present inventors have focused on the body coordination based on the co-activation of muscle pairs to analyze voluntary motions of humans.

The present inventors have searched for an effective intervention for sports coaching, fitness and rehabilitation, and extracted the body coordination (muscle synergy) with myogenic-potential signals during a voluntary motion as a motion-analyzing/evaluating tool to support the scientific ground. The present inventors then proposed a motion analyzing method of visualizing the motion strategy that the central nervous system selects for the implementation of the motion (manipulation of encoded low- and high-order parameters of the equilibrium-point trajectory, for example) (Patent Literature 1 and Non Patent Literature 1). The motion analyzing methods in Patent Literature 1 and Non Patent Literature 1 estimate the behavior of a muscle-group activity during a biological motion using the simplified models (assumptions) of: (1) muscles making up a musculoskeletal model have an equivalent size and balance; (2) various joints, such as shoulders and elbows, have the same moment arm; and (3) each muscle has a known myogenic potential during MVC (maximum voluntary contraction).

CITATION LIST

Patent Literature

Patent Literature 1: Patent Application Publication No. 2015-112453

Non Patent Literature

Non Patent Literature 1: H. Hirai, F. Miyazaki, H. Naritomi, K. Koba, T. Oku, K. Uno, M. Uemura, T. Nishi, M. Kageyama and H. I. Krebs, "On the Origin of Muscle Synergies: Invariant Balance in the Co-activation of Agonist and Antagonist Muscle Pairs." Front. Bioeng. Biotechnol., vol. 3, no. 192, pp. 1-16, 2015.

SUMMARY OF INVENTION

Technical Problem

The motion analyzing methods of Patent Literature 1 and Non Patent Literature 1 explain certain limited motions based on these simplified models. These methods, however, may not be sufficient to generalize biological motions. Particularly the assumption (3) has a practical limit for the purpose of rehabilitation. The maximum voluntary contraction (MVC) is a motion by a subject involving maximum voluntary efforts. This means that the MVC value as the output varies intra-individually or individually due to various external and internal factors, and such a variation may affect the result of the motion estimation. Such a motion with maximum voluntary contraction may become a burden to elderly or patients.

In view of the above, the present invention provides a motion analyzing device, a motion analyzing method, and a motion analyzing program that do not require a MVC motion for easy measurement of a motion and that improve the analysis accuracy.

Solution to Problem

A motion analyzing device according to the present invention includes: a myogenic potential detecting unit to detect a myogenic potential of a person who performs a motion; a motion detecting unit to detect a position of an endpoint of a limb of the person at a plurality of operating point positions; and a processor to calculate an equilibrium point of the person and a muscle synergy that is a set of base vectors describing the equilibrium point based on the myogenic potential detected by the myogenic potential detecting unit and the position of the endpoint of the limb detected by the motion detecting unit, the calculation being based on a musculoskeletal model of the person and a constraint condition that the position of the endpoint of the limb of the person matches the position of the equilibrium point in a static situation to keep a posture still under gravity compensation, wherein the processor includes: an agonist-antagonist (AA) muscle co-activation ratio (hereinafter referred to as an "AA muscle co-activation ratio") calculating means to calculate an AA muscle co-activation ratio based on the detected myogenic potential; a muscle synergy calculating means to calculate a muscle synergy based on the position of the endpoint of the limb detected by the motion detecting unit and the AA muscle co-activation ratio calculated by the AA muscle co-activation ratio calculating means; and an equilibrium point calculating means to calculate the equilibrium point based on the AA muscle co-activation ratio calculated by the AA muscle co-activation ratio calculating means, the position of the endpoint of the limb detected by the motion detecting unit, and the muscle synergy calculated by a muscle synergy calculating means.

A motion analyzing method according to the present invention includes: a myogenic potential detecting step of detecting a myogenic potential of a person who performs a motion; a motion detecting step of detecting a position of an endpoint of a limb of the person at a plurality of operating point positions; and a computing step of calculating an equilibrium point of the person and a muscle synergy that is a set of base vectors describing the equilibrium point based on the myogenic potential detected by the myogenic potential detecting step and the position of the endpoint of the limb detected by the motion detecting step, the calculation being based on a musculoskeletal model of the person and a constraint condition that the position of the endpoint of the limb of the person matches the position of the equilibrium point in a static situation to keep a posture still under gravity compensation, wherein the computing step includes: an AA muscle co-activation ratio calculating step of calculating an AA muscle co-activation ratio based on the detected myogenic potential; a muscle synergy calculating step of calculating a muscle synergy based on the position of the endpoint of the limb detected by the motion detecting step and the AA muscle co-activation ratio calculated by the AA muscle co-activation ratio calculating step; and an equilibrium point calculating step of calculating the equilibrium point based on the AA muscle co-activation ratio calculated by the AA muscle co-activation ratio calculating step, the position of the endpoint of the limb detected by the motion detecting step, and a muscle synergy calculated by the muscle synergy calculating step.

A motion analyzing program according to the present invention makes a motion analyzing device function as: a measurement instruction means to instruct a myogenic potential detecting unit to detect a myogenic potential of a person who performs a motion, and a motion detecting unit to detect a position of an endpoint of a limb of the person to detect a myogenic potential of the person and a position of the endpoint of the limb at a predetermined plurality of operating point positions; and a processor to calculate an equilibrium point of the person and a muscle synergy that is a set of base vectors describing the equilibrium point based on the myogenic potential detected by the myogenic potential detecting unit and the position of the endpoint of the limb detected by the motion detecting unit, the calculation being based on a musculoskeletal model of the person and a constraint condition that the position of the endpoint of the limb of the person matches the position of the equilibrium point in a static situation to keep a posture still under gravity compensation, wherein the processor includes: an AA muscle co-activation ratio calculating means to calculate an AA muscle co-activation ratio based on the detected myogenic potential; a muscle synergy calculating means to calculate a muscle synergy based on the position of the endpoint of the limb detected by the motion detecting unit and the AA muscle co-activation ratio calculated by the AA muscle co-activation ratio calculating means; and an equilibrium point calculating means to calculate the equilibrium point based on the AA muscle co-activation ratio calculated by the AA muscle co-activation ratio calculating means, the position of the endpoint of the limb detected by the motion detecting unit, and a muscle synergy calculated by the muscle synergy calculating means.

These aspects of the invention detect myogenic potentials of the person who performs the motion and the position of the limb endpoint. The processor calculates two feature amounts including the equilibrium point of the person and the muscle synergy that is a set of base vectors describing the equilibrium point from the detected information. Such calculation of the two feature amounts is performed based on the musculoskeletal model of the person and a constraint condition that the position of the endpoint of the limb of the person matches the position of the equilibrium point in a static situation to keep a posture still under gravity compensation. The muscle synergy calculating means of the processor calculates a set of muscle synergy vectors, and the equilibrium point calculating means calculates the equilibrium point. This eliminates the necessity of the MVC measurement as in the conventional method to simplify the motion measurement and improves the analysis accuracy.

BRIEF DESCRIPTION OF DRAWINGS

FIG. 2 shows muscles in an upper-limb musculoskeletal model and the coordinate system (radius R and angle Φ).

FIG. 5A to FIG. 5E shows experimental results of the motion analysis with subjects (A) to (E).

FIG. 6A shows the estimation results of the points on the inner circle, and FIG. 6B shows the estimation results of the points on the middle circle.

FIG. 8A and FIG. 8B describe the motion control with the musculoskeletal arm robot in FIG. 7, where FIG. 8A shows the motion control in the radial direction and FIG. 8B shows the motion control in the angular direction.

FIG. 10 shows the actual trajectory (Act) of the hand during a periodic reaching movement and deviations (De) between the hand position and the equilibrium point.

FIG. 11A and FIG. 11B show serial photographs of the periodic reaching movement in a horizontal plan view, where FIG. 11A shows the motion to the target position 2 and FIG. 11B shows the motion to the target position 5.

DESCRIPTION OF EMBODIMENTS

A motion analyzing method of the present invention estimates a motion command from the central nervous system with feature amounts including a muscle synergy and an equilibrium-point trajectory. The present invention considers a body motion by a person 1, a human in this example, who performs a motion, as a mechanical system (musculoskeletal model) having a musculoskeletal structure. Preferably the device stores the information on the musculoskeletal model in advance. The method measures the motion by the person 1 with the myogenic potential and the position of the operating point (hand, endpoint) of an upper limb, for example. As a result, the method obtains the musculoskeletal model, the myogenic potential and the position of the limb as the information on the person 1. The method then estimates and computes the feature amounts based on the information. When the body motion is considered in the mechanical system having a musculoskeletal structure, the feature amounts include the equilibrium point of the operating point (hand, endpoint) and the muscle synergy that is a set of base vectors describing the equilibrium point. These feature amounts can be analytically obtained based on the concept of the AA muscle co-activation ratio. The equilibrium point represents a position command from the central nervous system, and controls the operating point. The present embodiment describes the muscle synergy with components in the radial direction R and in the angular direction Φ (see FIG. 2).

Figure 1A:
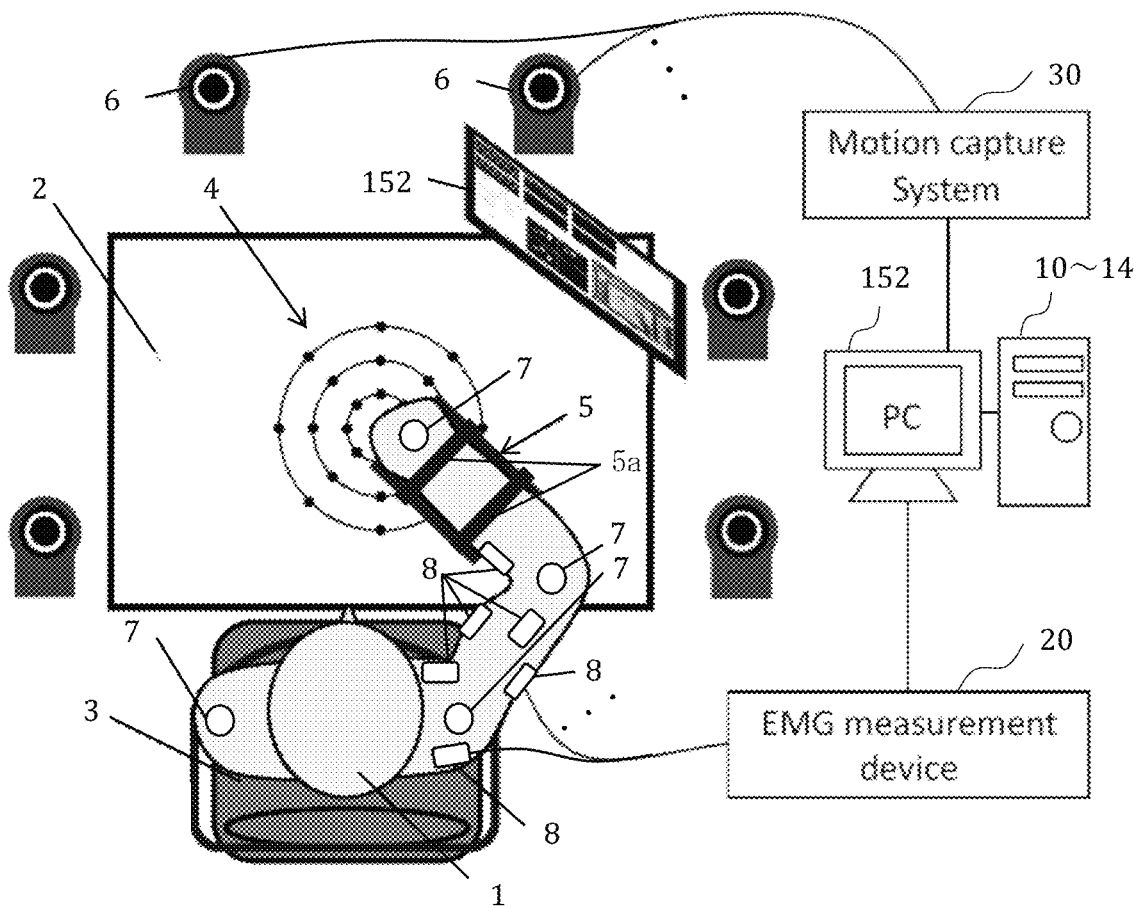
FIG. 1A shows the overall configuration of the motion analyzing device.
Figure 1B:
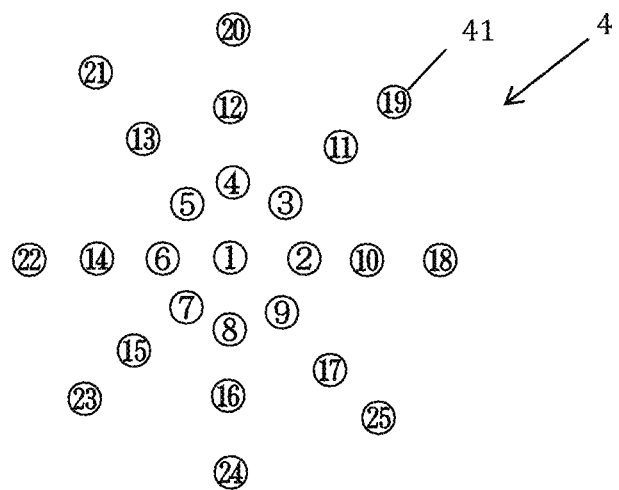
FIG. 1B is a chart showing one example of the operating point positions.

As shown in the horizontal plan view of FIG. 1A, the person 1 (subject) is seated on the chair 3 while facing the desk 2. The desk 2 has a top face in front of the person 1, on which a chart 4 showing the positions of the operating points is fixed. The chart 4 in one example includes a sheet, and has a plurality of operating-point positions 41 (see FIG. 1B) in a predetermined layout on the surface as described later. As shown in FIG. 1B, the chart 4 has a predetermined number, e.g., twenty-five operating-point positions 41. These operating-point positions 41 may have various layouts. As shown in FIG. 1B, the operating-points of the present embodiment include "1" at the center, "2" to "9" on the inner circle, "10" to "17" on the middle circle, and "18" to "25" on the outer circle. These circles have the radii of 5 cm, 10 cm, and 15 cm, from the center "1".

The right forearm of the person 1 is supported on a cart 5 and is fixed to a binder 5a. The cart 5 removes the gravitational effects on the right forearm of the person to be slidable on the desk 2. The means to remove the gravitational effects may be in the other forms instead of the cart 5, which may be a suspender, for example.

Muscles to be examined for motion analysis in this example include three-paired six muscles that play a major role in the upper-limb motion in a horizontal plane, and one pair of the muscles is a bi-articular muscle pair. FIG. 2 shows the muscles to be examined and the definitions of the coordination system. The cart 5 has a horizontally extending part, and has a grip (not shown) as a rod standing on the leading end of the horizontally extending part. The person 1 holds this grip with the right hand to fix the orientation of the wrist.

Figure 3:
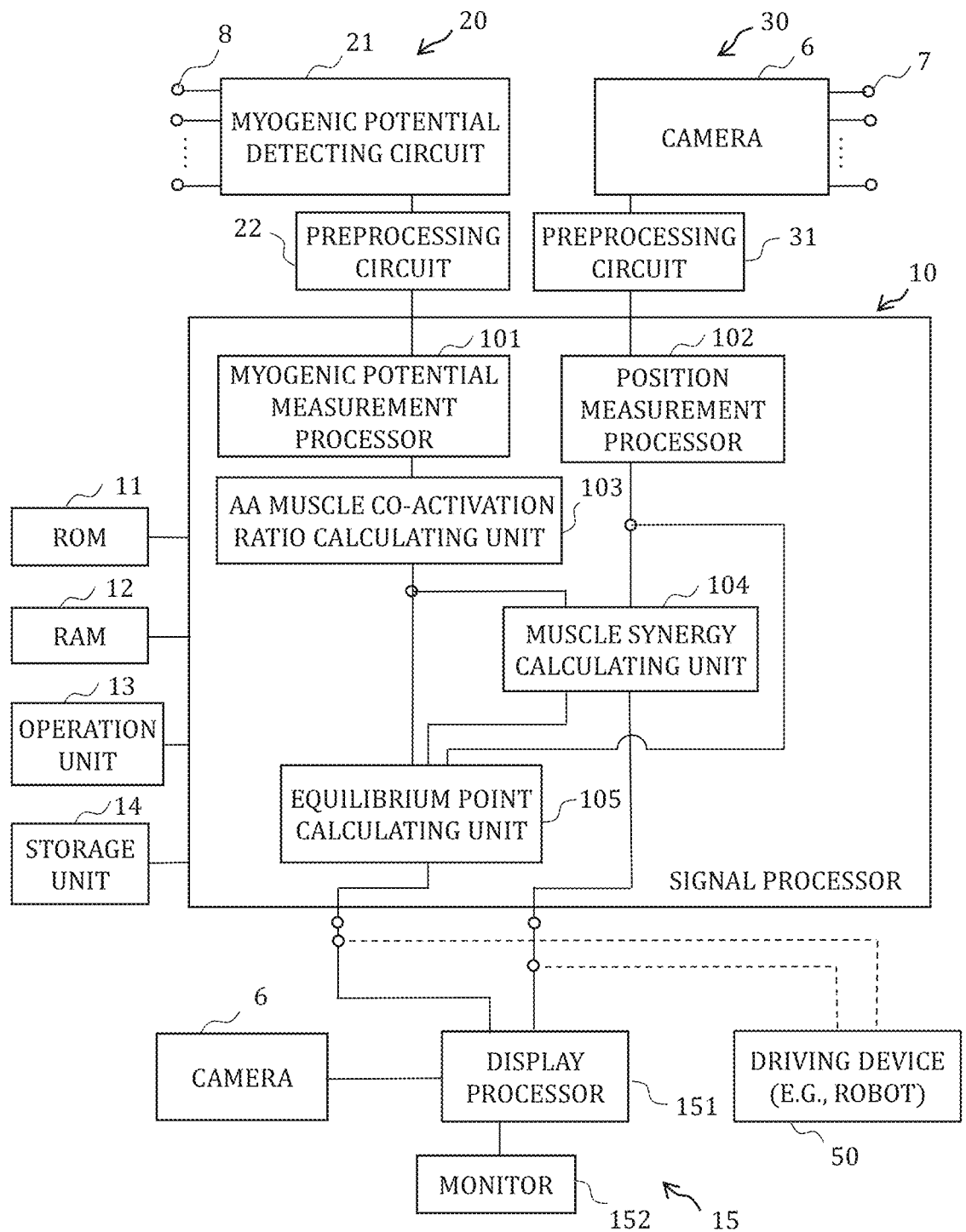
FIG. 3 is a block diagram showing one embodiment of the motion analyzing device.

The setup of the present embodiment includes an optical tracking system (Motion capture system 30, that is, position measuring unit 30), such as a motion capture, equipped with a camera 6 as an imaging means (see FIG. 3). In the present embodiment, markers 7 adhere to or are attached to the four positions in total, including the left shoulder, the right shoulder, and the right elbow at the center of their joints of the person 1 and the top of the above-stated grip as the rod so that the markers are observable from the above. In another example, the markers 7 maybe a member emitting a specific color, e.g., infrared light, or may be a light-emitting device. The camera 6 takes an image of each marker 7 as a bright point in the viewing field, and the bright points represent the positional information. Preferably the camera 6 takes an image downwardly from the right above of the chart 4 or from the right above or the vicinity of the right above of the person 1. These markers 7 at the left shoulder and the right shoulder at the center of their joints of the person 1 and marker 7 attached to the rod top of the grip at the cart 5 are used to measure the information on the angle Φ. The marker 7 attached to the rod top of the grip at the cart 5 shows the hand position of the right forearm of the person 1, and this marker 7 together with the marker 7 at the right shoulder of the person 1 are used to measure the information on the radius R. The rod-like grip of the cart 5 has the lower end extending toward the top face of the desk 2, and this allows the subject to visually position the grip on the chart 4 easily. The setup may include a laser pointer directed downward for positioning. The position measuring unit 30 performs the measurement. The setup may include other cameras 6 to take an image of the person 1 during the motion from desired multiple directions and so improve the accuracy of motion measurement. These other cameras are optional.

The person 1 wears a plurality of electrodes 8 attached on the skin of the right forearm. These electrodes 8 are attached on the surface of the muscles shown in FIG. 2 to detect the myogenic potential at the corresponding muscles. FIG. 2 shows the musculoskeletal system of the three-paired six muscles that mimics the human's upper-limb model, including deltoid posterior (ms,ext), deltoid anterior (ms,flx), long head of triceps brachii (mse,ext), biceps brachii (mse,flx), lateral head of triceps brachii (me,ext), and brachioradialis (me,flx). Muscles ms, ext and ms, flx, muscles mse, ext and mse, flx, and muscles me, ext and me, flx are pairs of antagonistic muscles. R and Φ in the drawing denote the radius and the angle in the polar coordinate system having the origin at the right shoulder.

Myogenic potentials are obtained by the measurement of EMG (electromyogram to directly measure a muscle activity (electromyography)), and introduce the concept of a ratio of activities between antagonistic muscles (AA muscle co-activation ratio) that are considered as a minimum unit for muscle coordination.

Referring back to FIG. 1A, the motion analyzing device includes: an EMG measurement device 20, that is, a myogenic potential measuring unit 20 to detect the myogenic potential of each electrode 8; a signal processor 10 to the storage unit 14 that make up a control unit of a personal computer; and a monitor 152.

Referring next to FIG. 3, the motion analyzing device includes: the myogenic potential measuring unit 20 to detect myogenic potentials of the person 1 via the electrodes 8; the position measuring unit 30 to detect the position of the motion via the markers 7 attached to the person 1; the signal processor 10 to perform predetermined signal processing based on the information obtained from these measuring units, and including a microcomputer, for example; and various parts 11 to 15 relating to the processing at the signal processor 10.

The myogenic potential measuring unit 20 includes six electrodes 8, a myogenic potential detecting circuit 21 to detect electrical signals generated at the electrodes 8, and a preprocessing circuit 22 to perform predetermined preprocessing to the detected electrical signals. The myogenic-potential signals obtained at the body surface are AC signals at the level of a few tens of μV to a few hundreds of μV in level and about 5 Hz to 500 Hz in frequency. The preprocessing circuit 22 includes an amplifier to amplify the myogenic potentials to a level that can be processed (a few thousands of times), a bandpass filter to transmit a signal of a major frequency band of the myogenic potentials only, and a full-wave rectifier circuit. The preprocessing circuit 22 includes an AD converter as well on the output side to enable digital-processing of the myogenic-potential signals.

The position measuring unit 30 includes the camera 6 located the right above to detect the markers 7, and a preprocessing circuit 31 to detect bright points based on the imaging signals from the camera 6 located the right above. The preprocessing circuit 31 performs predetermined pre-processing, such as measurement of positional coordinate information on the detected bright points. The position measuring unit 30 may be other known types of instrument including a magnetic generator and a magnetic sensor that can detect three-dimensional positions and directions, instead of the optical position-measuring unit.

The signal processor 10 includes a microcomputer having a CPU, and the motion analyzing device includes a ROM 11 to store a processing program for signal processing according to the present invention, a RAM 12 to temporarily store data being processed, an operation unit 13 including a numeric keypad or a mouse to issue a required command, and a storage unit 14. The storage unit 14 stores various types of arithmetic programs, data on the human-body musculoskeletal model, and other necessary data. The data on the human-body musculoskeletal model may be stored in a ROM 11 or a RAM 12.

The signal processor 10 connects to the display unit 15. The display unit 15 includes a display processor 151 and the monitor 152. The monitor 152 allows the user to check input information from the operation unit 13 or displays a processing result, and displays an image taken by the camera 6. The display processor 151 associates the processing result from the signal processor 10 with an image from the camera 6 and outputs the result to the display 152 to show this to the person 1 as needed.

The signal processor 10 executes a program read from the ROM 11 to the RAM 12, and so functions as: a myogenic potential measurement processor 101 to periodically execute measurement processing at the electrodes 8; a position measurement processor 102 to periodically execute measurement processing of the markers 7; an AA muscle co-activation ratio calculating unit 103 to calculate an AA muscle co-activation ratio from a signal obtained by the myogenic potential measurement processor 101; a muscle synergy calculating unit 104 to calculate muscle synergy from the outputs of the position measurement processor 102 and the AA muscle co-activation ratio calculating unit 103 and the data on the musculoskeletal model; and an equilibrium point calculating unit 105 to calculate an equilibrium point from the outputs of the position measurement processor 102, the AA muscle co-activation ratio calculating unit 103 and the muscle synergy calculating unit 104. The myogenic potential measurement processor 101 and the position measurement processor 102 perform the measurement in synchronization to acquire the mutually associated information. The following describes a method for motion analysis in association with the descriptions of these functions.

According to a conventional analyzing method, let that the position of the equilibrium point in the radial direction and in the angular direction at the operating point is $p_{EP} = (R_{EP}, \Phi_{EP})^T$, the displacement $\Delta p_{EP}$ is represented as the linear combination of the function (muscle synergy) $S^T$ and the deviation $\Delta r_j$, (j=s,se,e) of the AA muscle co-activation ratio by equation (1). See "Muscle Synergies, Equilibrium-point Trajectory and Endpoint Stiffness during Human Upper-limb Movements on a Horizontal Plane: an Approach using EMG Signals", by Kanna Uno, Takanori Oku, Keitaro Koba, Mitsunori Uemura, Hiroaki Hirai and Fumio Miyazaki, Journal of the Robotics Society of Japan, vol. 32, no. 7, pp. 603-614, 2014.

[Mathematical 1]

$$\begin{bmatrix} \Delta R_{EP} \\ \Delta \Phi_{EP} \end{bmatrix} = \underbrace{\begin{bmatrix} C_R & 0 \\ 0 & C_\Phi \end{bmatrix} S^T \begin{bmatrix} \Delta r_s \\ \Delta r_{se} \\ \Delta r_e \end{bmatrix}}_{(A)} \quad (1)$$

Note here that muscle synergy $S^T$ includes muscle synergy vectors of $[S_{R,s}\ S_{R,se}\ S_{R,e}]$ and $[S_{\Phi,s}\ S_{\Phi,se}\ S_{\Phi,e}]$ in the radial direction and in the angular direction, and is represented by the balance of joint stiffness due to the co-activation of antagonistic muscles. $[\Delta r_s\ \Delta r_{se}\ \Delta r_e]^T$ denotes a deviation from the time sample mean of each AA muscle co-activation ratio $r_j$, (j=s,se,e), and $C_R$, $C_\Phi$ are constants depending on the characteristics of the musculoskeletal system (characteristics of each muscle, the link length and the diameter of the moment arm of the joint). The index T of the above matrix denotes the transposed matrix.

In contrast, the analyzing method of the present invention obtains Eq. 5 to represent $[\Delta r_s\ \Delta r_{se}\ \Delta r_e]^T$ in the above Eq. 1 using the EMG (myogenic potential) $m_{j,ext}, m_{j,flx}$ and the MVC value $M_{j,ext}, M_{j,flx}$, (j=s,se,e) of each antagonistic-muscles pair when the muscles keep the posture still (i.e., in the static situation) and through Eq. 2, Eq. 3, and Eq. 4.

[Mathematical 2]

$$M'_j = \frac{M_{j,ext}}{M_{j,flx}} \quad T'_j = \frac{m_{j,ext}}{m_{j,flx}} \quad (j = s, se, e) \quad (2)$$

$$r_j = \frac{r'_j}{r'_j + M'_j} \quad (3)$$

$$r_i^2 \approx \frac{1}{M'_j} \cdot \frac{r'_j}{4} \quad (4)$$

$$r_i \approx \frac{1}{\sqrt{M'_j}} \cdot \frac{\sqrt{r'_j}}{2} \quad (5)$$

Inserting Eq. 5 into Eq. 1 leads to the following Eq. 6.

[Mathematical 3]

$$\begin{bmatrix} \Delta R_{EP} \\ \Delta \Phi_{EP} \end{bmatrix} \approx \underbrace{\begin{bmatrix} C_R & 0 \\ 0 & C_\Phi \end{bmatrix}}_{(B:\ Unkown\ parameters)} S^T \underbrace{\begin{bmatrix} \frac{1}{\sqrt{M'_s}} & 0 & 0 \\ 0 & \frac{1}{\sqrt{M'_{se}}} & 0 \\ 0 & 0 & \frac{1}{\sqrt{M'_e}} \end{bmatrix}}^{(A)} \underbrace{\begin{bmatrix} \Delta \frac{\sqrt{r'_s}}{2} \\ \Delta \frac{\sqrt{r'_{se}}}{2} \\ \Delta \frac{\sqrt{r'_e}}{2} \end{bmatrix}}_{(C:\ measurable\ parameters)} \quad (6)$$

$$= \underbrace{S'^T}_{(B:\ Unknown\ parameters)} \begin{bmatrix} \Delta \frac{\sqrt{r'_s}}{2} \\ \Delta \frac{\sqrt{r'_{se}}}{2} \\ \Delta \frac{\sqrt{r'_e}}{2} \end{bmatrix} \quad (7)$$

All of the parameters in Eq. 1 are unknown, and the term (A) at the end corresponds to the third term and the fourth term on the right side of Eq. 6. The fourth term includes measurable parameters. The term (B) in this equation remains as unknown parameters, and Eq. 7 has this collectively as $S'^T$.

Substituting Eq. 7 to find $S'^T$ leads to Eq. 8. The index # of the matrix denotes the pseudo-inverse matrix.

[Mathematical 4]

$$S'^T \approx \begin{bmatrix} \Delta R_{EP} \\ \Delta \Phi_{EP} \end{bmatrix} \begin{bmatrix} \Delta\frac{\sqrt{r'_s}}{2} \\ \Delta\frac{\sqrt{r'_{se}}}{2} \\ \Delta\frac{\sqrt{r'_e}}{2} \end{bmatrix}^{\#} \quad (8)$$

Endpoint position matches equilibrium point position in the static situation.

$$\begin{bmatrix} R_{EP} \\ \Phi_{EP} \end{bmatrix} = \begin{bmatrix} R \\ \Phi \end{bmatrix} \quad (9)$$

$$S'^T \approx \begin{bmatrix} \Delta R \\ \Delta \Phi \end{bmatrix} \begin{bmatrix} \Delta\frac{\sqrt{r'_s}}{2} \\ \Delta\frac{\sqrt{r'_{se}}}{2} \\ \Delta\frac{\sqrt{r'_e}}{2} \end{bmatrix}^{\#} \quad (10)$$

Note here that the equilibrium point of the hand matches the endpoint position when keeping the posture still (in the static situation) on a horizontal plane. Since Eq. 9 holds based on this physical constraint condition, applying this relationship to Eq. 8 leads to Eq. 10.

The analyzing method of the present invention performs the measurement with the myogenic potential measuring unit 20 and the position measuring unit 30 while keeping the hand of the person 1 still at a predetermined position on the chart 4. For the measurement, the person 1 moves the hand on the chart 4 sequentially from the operating point "1" to the operating point "25", for example. Once the hand reaches a certain operating point, the person keeps the hand still at the operating point. While keeping the hand there, the myogenic potential measuring unit 20 and the position measuring unit 30 perform the measurement in response to a measurement instruction received from the signal processor 10, for example. When the measurement at the operating point ends, the person moves the hand to the next operating point. Then the measurement is performed similarly while keeping the hand still. The person then repeats a similar operation till the final operating point "25".

Eq. 11 shows the case of extending the operating points to 1 to n (twenty-five points in this example), and Eq. 12 shows the extension of Eq. 10.

[Mathematical 5]

Based on endpoint position at point $n$ and myogenic information $$\begin{bmatrix} \Delta R_1 & \cdots & \Delta R_n \\ \Delta \Phi_1 & \cdots & \Delta \Phi_n \end{bmatrix} \approx S'^T \begin{bmatrix} \Delta\left(\frac{\sqrt{r'_{s,1}}}{2}\right) & \cdots & \Delta\left(\frac{\sqrt{r'_{s,n}}}{2}\right) \\ \Delta\left(\frac{\sqrt{r'_{se,1}}}{2}\right) & \cdots & \Delta\left(\frac{\sqrt{r'_{se,n}}}{2}\right) \\ \Delta\left(\frac{\sqrt{r'_{e,1}}}{2}\right) & \cdots & \Delta\left(\frac{\sqrt{r'_{e,n}}}{2}\right) \end{bmatrix} \quad (11)$$

$$S'^T \approx \begin{bmatrix} \Delta R_1 & \cdots & \Delta R_n \\ \Delta \Phi_1 & \cdots & \Delta \Phi_n \end{bmatrix} \begin{bmatrix} \Delta\left(\frac{\sqrt{r'_{s,1}}}{2}\right) & \cdots & \Delta\left(\frac{\sqrt{r'_{s,n}}}{2}\right) \\ \Delta\left(\frac{\sqrt{r'_{se,1}}}{2}\right) & \cdots & \Delta\left(\frac{\sqrt{r'_{se,n}}}{2}\right) \\ \Delta\left(\frac{\sqrt{r'_{e,1}}}{2}\right) & \cdots & \Delta\left(\frac{\sqrt{r'_{e,n}}}{2}\right) \end{bmatrix}^{\#} \quad (12)$$

$\Delta$ denotes the displacement from their time sample mean. Although the descriptions are omitted, muscle synergies can be represented by Eq. 13 and Eq. 14 through several algebraic steps. Once $S'^T$ is known, values A and B also can be found, whereby muscle synergies $S^T$ will be found. In this way, the constraint condition can be used to derive feasible muscle synergies by statistically estimating the term B as the unknown parameters in Eq. 7.

[Mathematical 6]

$$S^T = \frac{1}{A+B+AB}\begin{bmatrix} -A & A & B+AB \\ \frac{A}{2}+AB & \frac{A}{2}+B & -\frac{B}{2}+\frac{AB}{2} \end{bmatrix} \quad (13)$$

$$A = \frac{-\frac{S'_{\Phi,s}}{S'_{R,s}} + \frac{S'_{\Phi,e}}{S'_{R,e}}}{\frac{S'_{\Phi,se}}{S'_{R,se}} - \frac{S'_{\Phi,e}}{S'_{R,e}}}$$

$$B = \frac{-\left(\frac{S'_{\Phi,s}}{S'_{R,s}} + \frac{S'_{\Phi,se}}{S'_{R,se}}\right)\left(\frac{S'_{\Phi,s}}{S'_{R,s}} - \frac{S'_{\Phi,e}}{S'_{R,e}}\right)}{2\left(\frac{S'_{\Phi,s}}{S'_{R,s}} - \frac{S'_{\Phi,se}}{S'_{R,se}}\right)\frac{S'_{\Phi,e}}{S'_{R,e}}} \quad (14)$$

Note here that Eq. 13 does not include $M'_j$, (j=s,se,e). In other words, the present method does not need to measure the MVC in advance by muscle testing Helen J. Hislop, Jacqueline Montgomery, Daniels and Worthingham's Muscle Testing: Techniques of Manual Examination, 8th edition, Elsevier Inc., New York, N.Y., USA, 2007), for example. This method has another advantage of estimating muscle synergies with consideration given to the muscle-power balance specific to the examined person through statistical analysis.

The present method analyzes the motion using myogenic potentials when keeping the posture still and does not need a relatively large muscular force unlike the MVC measurement. The present method also is based on the universal physical relationship (the constraint condition as stated above) between the position of the endpoint and the position of the equilibrium point when keeping the posture still. In this way, the present method solves the problems in the conventional technique. The analyzing device by this method is therefore practical. Especially the elimination of the MVC measurement contributes to the advantages of easing the testing procedure, improving the estimation accuracy, and reducing the burden on the subject.

A driving robot 50 shown in FIG. 3 includes a plurality of actuators to move required parts of a mechanism, for example. This driving robot is made up of McKibben-type artificial muscles, for example, enabling adjustment of the air pressure in accordance with an electrical signal so as to expand or contract a pneumatic rubber tube, and receives (transplanted) a signal in accordance with the feature amounts for operation. The actuators are not limited to the McKibben-type artificial muscles, which may be other electromechanical conversion elements that covert an electrical signal or another force converted from an electrical signal into a mechanical motion, such as an electromagnetic solenoid, a piezoelectric element and a motor. When a control target is a musculoskeletal robot having an artificial-muscle arm, e.g., an upper-limb musculoskeletal robot, a mechanism to create an artificial muscle activity command to implement a target hand motion is required similarly to the motion of a human body.

Figure 4:
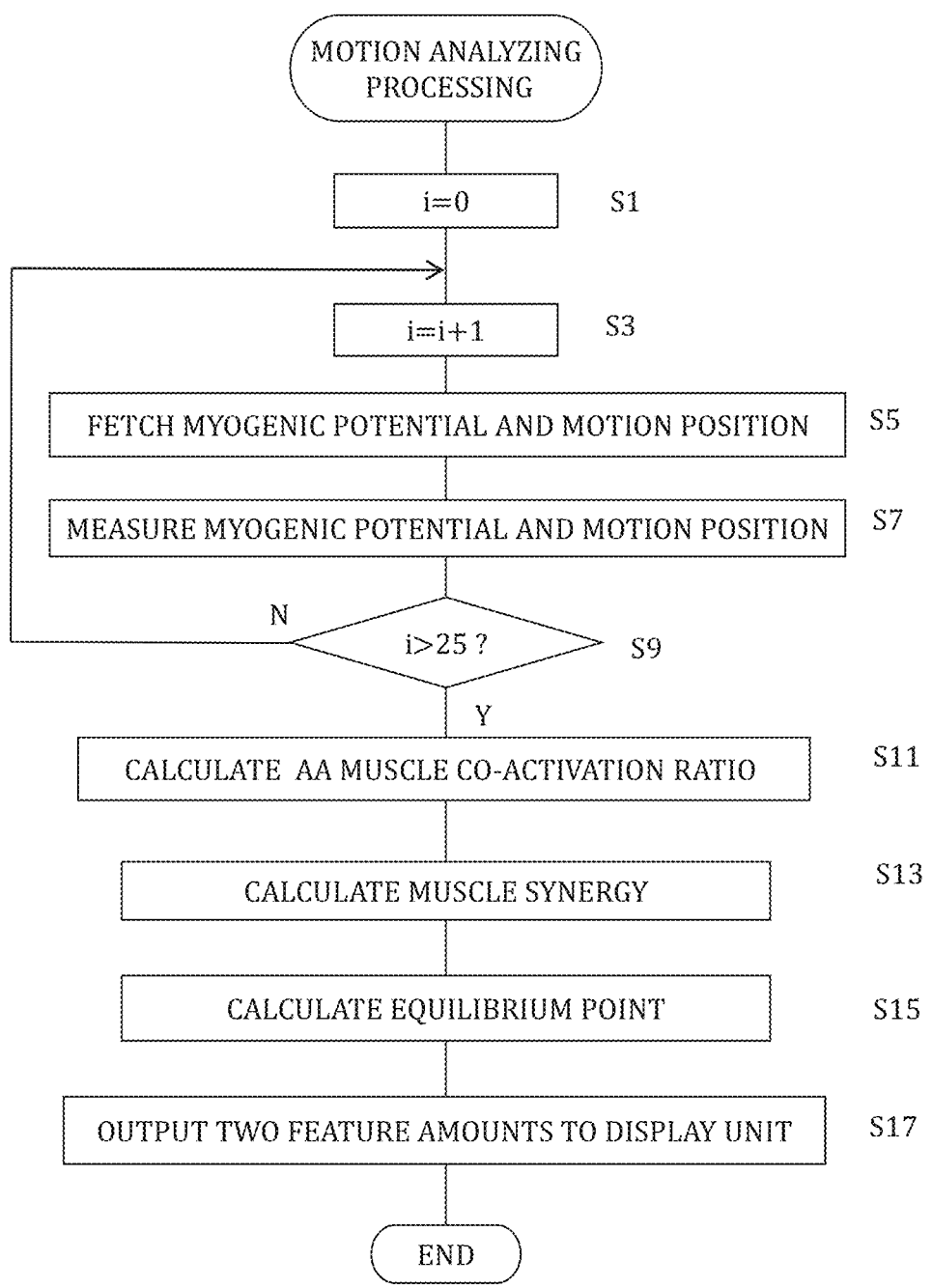
FIG. 4 is a flowchart showing one embodiment of the procedure for the motion analysis.

FIG. 4 is a flowchart showing the procedure for motion analysis processing. Firstly, the procedure sets parameter i representing the number of the operating point as i=0 (Step S1). Next, the procedure increments parameter i by one (Step S3) and fetches detection signals of myogenic potentials and signals of motion positions for the first operating point from the myogenic potential measuring unit 20 and the position measuring unit 30 (Step S5) and executes the measurement processing of myogenic potentials and the measurement processing of the motion positions based on these signals (Step S7).

Next the procedure determines whether the measurement processing ends or not for the parameters i>25, i.e., all of the operating points (e.g., twenty-five points) (Step S9). If the measurement processing does not end, the procedure returns to Step S3 to move the hand to the next operating point. After confirming the hand being kept still, the procedure executes the measurement processing in response to a manual measurement instruction, for example. If the measurement processing ends, the procedure calculates the AA muscle co-activation ratio for each antagonistic muscles based on the myogenic-potential signals measured at all of the operating points (Step S11).

Subsequently the procedure, i.e., the muscle synergy calculating unit 104, calculates muscle synergies that are one of the feature amounts based on the information on the AA muscle co-activation ratio and the motion positions and the data on the musculoskeletal model (Step S13). Next the procedure, i.e., the equilibrium point calculating unit 105, calculates the equilibrium point that is the other feature amount based on the information on the AA muscle co-activation ratio, the motion positions and the muscle synergies (Step S15). The procedure outputs these calculated two feature amounts to the display processor 151 (Step S17) to display them on the monitor 152.

The following describes Experiment I to verify the effects.

(1) Experiment I

The experimental setup was the device shown in FIG. 1A. Each of five subjects (A to E) was instructed to move the hand sequentially from the first to the twenty-fifth points on the chart 4 while using the device shown in FIG. 1A, and keep the hand still at each of the points. While the subject was keeping the hand still, EMG of each muscle and the hand position were measured by the myogenic potential measuring unit 20 and the position measuring unit 30. Such measurement by the myogenic potential measuring unit 20 and the position measuring unit 30 of the subject who keeping the posture still at the predetermined positions was performed in 10 seconds and at 100 Hz in one example.

(2) Results

In FIG. 5A to FIG. 5E, the upper drawings (a) show muscle synergies during the motion of each subject, and the lower drawings (b) show the endpoints and the corresponding equilibrium points at the operating points (first to twenty-fifth points). The bars representing muscle synergies show the radial R-direction component on the left and the angular-$\Phi$ direction component on the right, and show the components for Shoulder, Shoulder & Elbow, and Elbow.

Figure 6A:
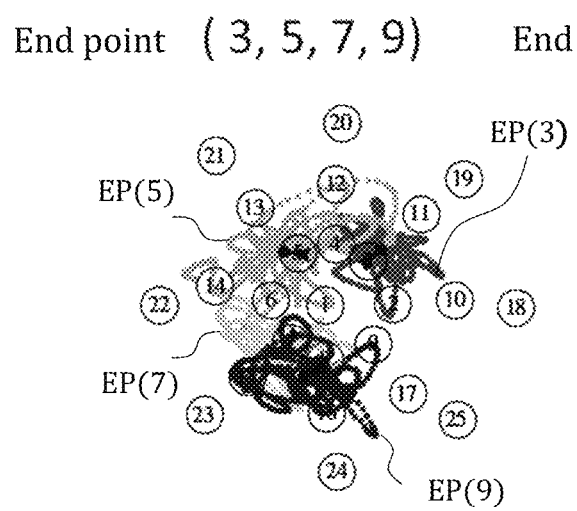
FIGS. 6A and 6B show the estimation results of the variability of equilibrium points, where
Figure 6B:
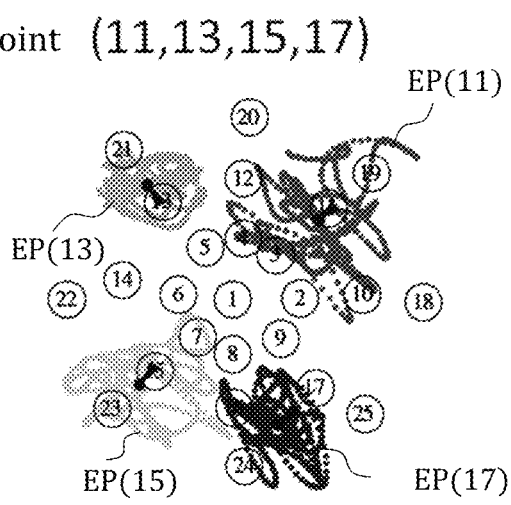

The equilibrium point was calculated using the muscle synergies and the AA muscle co-activation ratio. FIG. 5A to FIG. 5E show that the muscle synergy vectors estimated in this experiment had the same sign but had different balance from the muscle synergy vectors estimated by the conventional method ("Muscle Synergies, Equilibrium-point Trajectory and Endpoint Stiffness during Human Upper-limb Movements on a Horizontal Plane: an Approach using EMG Signals", by Kanna Uno, Takanori Oku, Keitaro Koba, Mitsunori Uemura, Hiroaki Hirai and Fumio Miyazaki, Journal of the Robotics Society of Japan, vol. 32, no. 7, pp. 603-614, 2014). FIG. 5A to FIG. 5E show that the endpoint and the equilibrium point are generally close to each other. The equilibrium points shown are the average of a plurality of measurements with consideration given to the variability (fluctuations) of the equilibrium points as shown in FIG. 6A and FIG. 6B, for example.

(3) Discussion

The estimated muscle synergy vectors were obtained with consideration given to the muscle-power balance specific to the examined person, and so had a different balance from the result by the conventional method. The conventional method assumes that all of the muscles are equivalent.

The estimated muscle synergies were calculated as feasible values that describe the motion based on the statistic data analysis and without implausible data analysis. This result therefore contributes to (1) good understanding of a human motion of controlling the redundant muscle groups, (2) assessment of an exercise targeted to rehabilitation, and (3) development of the motion control of a robot that mimics the human's musculoskeletal structure.

As shown in Table 1, the muscle synergy vectors of subjects A to E extracted by this analysis method highly matched among these five subjects (inner product values were 0.996±0.005 in the radial R direction, and 0.987±0.017 in the angular $\phi$ direction).

TABLE 1

ELEMENT VALUES OF SYNERGY VECTORS

| | $S_R^T = [S_{R,s}\ S_{R,se}\ S_{R,e}]$ | | | $S_\Phi^T = [S_{\Phi,s}\ S_{\Phi,se}\ S_{\Phi,e}]$ | | |
|---|---|---|---|---|---|---|
| Subject | Shoulder | Shoulder and elbow | Elbow | Shoulder | Shoulder and elbow | Elbow |
| A | −0.707 | 0.707 | 0.020 | 0.595 | 0.798 | −0.102 |
| B | −0.703 | 0.703 | −0.114 | 0.397 | 0.885 | −0.244 |
| C | −0.700 | 0.700 | −0.142 | 0.561 | 0.188 | −0.129 |
| D | −0.707 | 0.707 | 0.032 | 0.603 | 0.792 | −0.094 |
| E | −0.707 | 0.707 | −0.034 | 0.384 | 0.888 | −0.252 |
| mean | −0.705 | 0.705 | −0.048 | 0.508 | 0.836 | −0.164 |
| | (±0.003) | (±0.003) | (±0.078) | (±0.109) | (±0.047) | (±0.078) |

TABLE II

INNER-PRODUCT VALUES BETWEEN SYNERGY VECTORS

| | $S_R^T$ | $S_\Phi^T$ |
|---|---|---|
| Inter-individual variations | 0.996 | 0.987 |
| | (±0.005) | (±0.017) |

This shows that this method to extract muscle synergies hardly reflect inter-individual variations among the subjects, i.e., is high in generality.

FIG. 6A and FIG. 6B show an example of the variability (fluctuations) of the equilibrium points for a plurality of operating points. FIG. 6A shows the variability of the equilibrium points at the operating points 3, 5, 7 and 9 on the inner circle (EP(3), EP(5), EP(7), and EP(9) in the drawing), and FIG. 6B shows the variability of the equilibrium points at the operating points 11, 13, 15 and 17 on the middle circle (EP(11), EP(13), EP(15), and EP(17) in the drawing).

The equilibrium point for an operating point is a biosignal that reflects a motion command originating from the central nervous system to implement a desired motion, and so has variability. Such variability can be considered as the changing trend of the feature amount relative to the motion command. The variability appears as the fluctuation degree of the equilibrium point, which may relate to the symptoms of the patient or the recovery status of the patient (including rehabilitation). Observation of the variability and of a change of the variability over time therefore may be used for the diagnosis and treatment of movement.

The equilibrium point calculating unit 105 may calculate the equilibrium point for each operating point based on a plurality of pieces of measurement information, and may display the calculated equilibrium points through the display processor 151 on the monitor 152 as shown in FIG. 6A and FIG. 6B.

Figure 7:
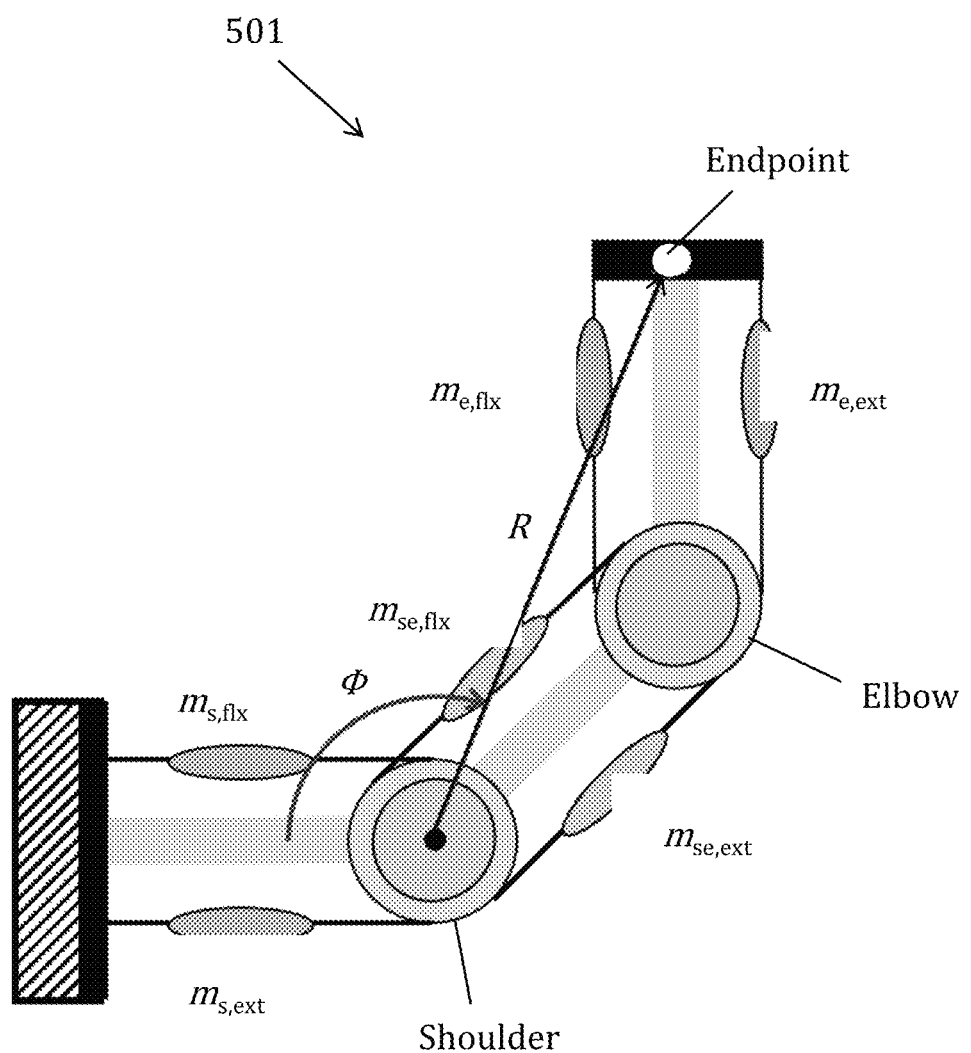
FIG. 7 illustrates a musculoskeletal arm robot that mimics an upper limb.

The following describes the verification for the estimated muscle synergy vectors using a musculoskeletal arm robot having three-paired six muscles that mimics a human upper limb model. For the musculoskeletal arm robot 501, the driving robot 50 shown in FIG. 3 was used in this case. More specifically as shown in FIG. 7, the musculoskeletal arm robot 501 includes muscles $m_{s,ext}$ and $m_{s,\ flx}$ between the fixing part and the shoulder, muscles $m_{se,ext}$ and $m_{se,\ flx}$ between the shoulder and the elbow, and muscles $m_{e,\ ext}$ and $m_{e,\ flx}$ between the elbow and the hand (endpoint).

More detailed configuration is as follows:
Moment arm: 48 mm for all;
Arm length: 264 mm for all;
Overall mass: 1.7 kg;
Artificial muscles: McKibben-type pneumatic artificial muscles (type 1.0 inch produced Kanda Tsushin Kogyo Co., Ltd., Japan) for all;
Pneumatic controller: pneumatic servo system produced by Festo Co.;
Air compressor: JUN-AIR, JUNAIR12-25; and
DA board: PCI-3346A, PCI3522A (Interface Co., Ltd.).

The pneumatic pressure was controlled by the pneumatic controller. This pneumatic controller was equipped with a servo electromagnetic valve that controls the pneumatic pressure in accordance with the input voltage. The pneumatic controller receives a command voltage from the computer via the DA board to control the supply voltage. The compressed air was supplied by the air compressor.

The radial R components [$S_{R,s}\ S_{R,se}\ S_{R,e}$] and the angular Φ components [$S_{\Phi,s}\ S_{\Phi,se}\ S_{\Phi,e}$] of muscle synergy $S^T$ were transplanted to the musculoskeletal arm robot 501, and the displacement of the hand was measured while controlling the muscle-synergy activation coefficients in the radial/angular directions.

FIG. 8A and FIG. 8B show the results obtained while controlling the muscle-synergy activation coefficients in the radial/angular directions. Such individual control of the muscle-synergy activation coefficients in these directions enabled a substantially linear movement of the musculoskeletal arm robot 501 in the selected direction.

FIG. 8A shows the muscle synergy vectors [$S_{R,s}\ S_{R,se}\ S_{R,e}$] controlled in the radial direction, where (1) shows the synergy activation coefficient $W_\Phi$=−0.2, (2) shows the synergy activation coefficient $W_\Phi$=0, and (3) shows the synergy activation coefficient $W_\Phi$=0.2. While $W_R$ was controlled linearly, $W_\Phi$ was constant. FIG. 8B shows the muscle synergy vectors [$S_{\Phi,s}\ S_{\Phi,se}\ S_{\Phi,e}$] controlled in the angular direction, where (1) shows the synergy activation coefficient $W_R$=−0.2, (2) shows the synergy activation coefficient $W_R$=0, and (3) shows the synergy activation coefficient $W_R$=0.2. While $W_\Phi$ was controlled linearly, $W_R$ was constant. The results of FIGS. 8A and 8B show the validity of this method, and shows that the estimated muscle synergy vectors correctly operated in the radial and angular directions. The drawings on the left of FIGS. 8A and 8B show one example of the movement trajectory of the three operating points (hand, endpoint) when the synergy activation coefficient $W_\Phi$ and the synergy activation coefficient $W_R$ had certain values.

The synergy activation coefficients $W_R$ and $W_\Phi$ in the above were obtained by Eq. 15. The equilibrium points $R_{EP}$ and $\Phi_{EP}$ were estimated by Eq. 16 using the synergy activation coefficients $W_R$ and $W_\Phi$. In the equation, $K_R$ and $K_\Phi$ denote gain coefficients, and $R_0$ and $\Phi_0$ denote the initial positions as the time sample mean.

[Mathematical 7]

$$\begin{bmatrix} w_R \\ w_\Phi \end{bmatrix} = S'^T \begin{bmatrix} \Delta\left(\dfrac{\sqrt{r'_s}}{2}\right) \\ \Delta\left(\dfrac{\sqrt{r'_{se}}}{2}\right) \\ \Delta\left(\dfrac{\sqrt{r'_e}}{2}\right) \end{bmatrix} \quad (15)$$

[Mathematical 8]

$$\left. \begin{array}{l} R_{EP} = k_R w_R + R_0 \\ \Phi_{EP} = k_\Phi w_\Phi + \Phi_0 \end{array} \right\} \quad (16)$$

The above Experiment I was to verify the effect of estimating the equilibrium points in the static situation. The following describes Experiment II to verify the effect of estimating the equilibrium points during a motion.

(1) Experiment II

The experimental setup was the device shown in FIG. 1A. The experiment was conducted for each of five subjects (A to E) using the device shown in FIG. 1A. A chart 40 shown in FIG. was used in this experiment. This chart 40 included large-sized numerals 0 to 8 added at the center position of the chart 4 and the target positions on the outermost circle in FIG. 1B.

(2) Procedure

The motion was a typical periodic reaching movement. The motion in Experiment II was the reaching movement (reciprocal motion) between the center position 0 indicated with the large-sized numeral 0 and the target positions 1 to 8 indicated with the numerals 1 to 8 on the chart 40. Each subject performed a continuous reaching movement between the center position 0 and each of the target positions 1 to 8. More specifically the reaching movement started with the reciprocal motion between the center position 0 and the target position 1, and the subject continuously performed such a motion while sequentially changing the motion between the center position 0 and the target positions 2, 3 . . . 8. A metronome was keeping the tempo of the motion to the target position and the motion to the center position at a typical speed, e.g., 60 or 80 bmp.

(3) Algorithm

Firstly the muscle synergy $S'^T$ at the operation point 1 at the center and the operating points 18 to 25 (the same positions as the center position 0 and the target positions 1 to 8 in Experiment II) was estimated in Experiment I while keeping the posture still. Muscle synergy does not change between during keeping the posture still and during a motion. Based on this, the equilibrium point during the motion was estimated by the equilibrium point calculating unit 105 using the muscle synergy $S'^T$ estimated by Experiment I in the static situation and the AA muscle co-activation ratio $r'_j$ obtained during the reaching movement in Experiment II and by Eq. 15 and Eq. 16. The algorithm is basically the same as the case of keeping the posture still, and is different in that the AA muscle co-activation ratio $r'_j$ to be used is replaced from the AA muscle co-activation ratio during keeping the posture still to the AA muscle co-activation ratio during the reaching movement.

(3) Results

FIG. 10 shows the reciprocal actual trajectory Act between the center position 0 and each of the target positions 1 to 8 during the periodic reaching movement, and the equilibrium-point trajectory De obtained periodically during the reaching movement. The actual trajectory Act represents the actual trajectory of the hand, and the equilibrium-point trajectory De indicated with arrows represents the deviations from the hand position at the equilibrium points. FIG. 11A and FIG. 11B show a horizontal plan view of the serial photographs of the subject 1 during the periodic reaching movement. FIG. 11A shows one reciprocal motion between the center position 0 and the target position 2, and FIG. 11B shows one reciprocal motion between the center position 0 and the target position 5. The time interval between the adjacent photographs was 0.4 msec., for example. In this drawing, hp denotes the hand position of subject 1 and ep denotes the equilibrium point . This shows that the equilibrium point ep leads the hand position hp so that the motion is planned to compensate for the dynamical influences on the hand. These features in FIG. 10 and FIGS. 11A and 11B were common to the other subjects as well.

(4) Discussion

During the periodic reaching movement, the equilibrium-point trajectory was distorted so that the actual trajectory Act of the hand, which was dynamically affected from the motion, satisfied the linearity. The arrows De indicating the equilibrium points in FIG. 10 show this. That is, although the arrows De are directed in the target direction roughly, the direction is slightly deviated in each motion phase (e.g., the early phase, the intermediate phase and the later phase in the reaching movement from the center position 0 to any target position). This result shows that the equilibrium-point trajectory De is planned in advance so that the actual trajectory Act affected dynamically during the motion meets desired conditions, such as having linearity. To this end, the equilibrium-point trajectory De leads the actual trajectory Act in the motion. In other words, this suggests that the central nervous system of a human creates an internal model for the dynamic environment to control the motion, and accordingly makes a motion plan. The present invention visualizes the internal processing (muscle synergy and equilibrium-point trajectory). Non Patent Literature 1, for example, describes how the muscle synergy and the equilibrium-point trajectory of a stroke patient changed to recover. The present invention enables a similar analysis easily and without measuring the MVC value, and so is effective for the motion assessment and the treatment in clinical practice.

Figure 9:
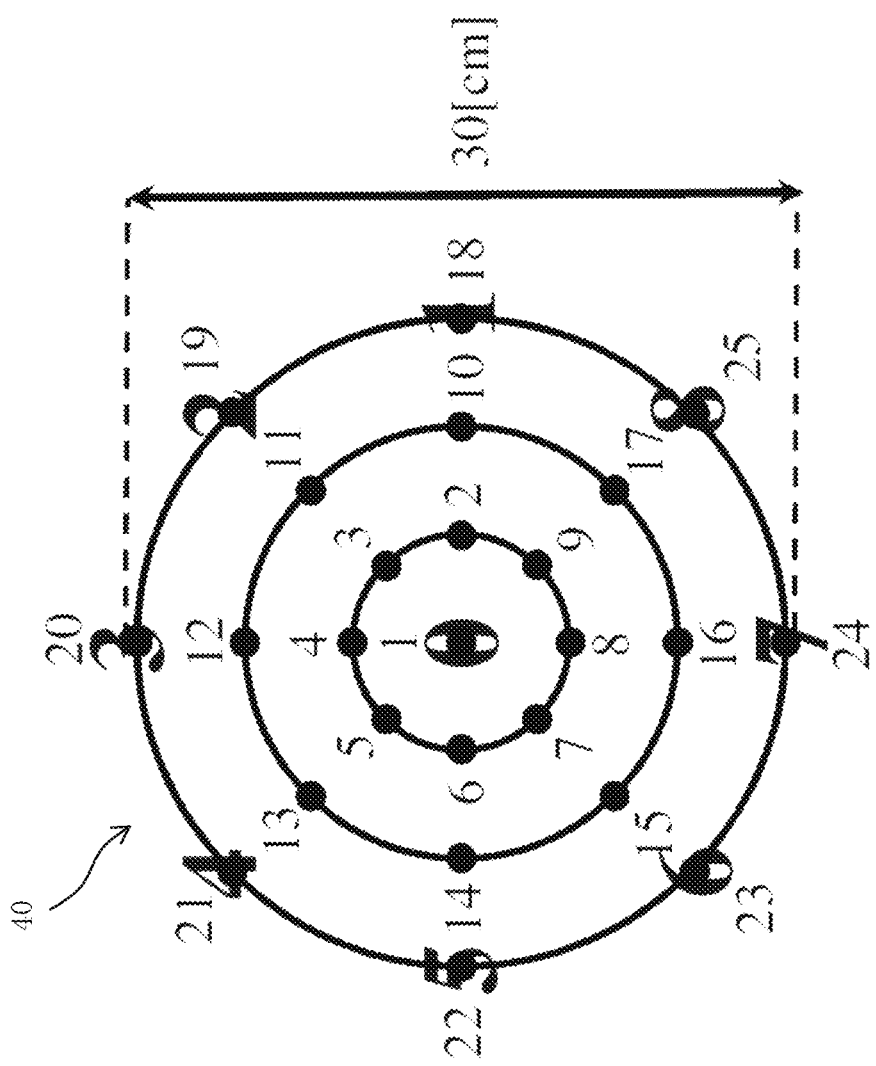
FIG. 9 shows target positions for a motion task, where black points 1 to 25 (twenty-five points) indicate the target positions to keep the posture still, and large-sized numerals 0 to 8 (nine points) indicate the target positions for a periodic reaching movement.

The present embodiment and Experiments I and II illustrate non-limiting examples of the number of the operating points and their layout as in FIG. 1B and FIG. 9, which may be other numbers and layouts. In one example, the operating points may be disposed at random as long as the number of the operating points is enough to uniformly cover a desired motion range of the limb.

The above embodiment describes the upper-limb motion on the desk. A body part to move may be a lower limb instead of the upper limb, or the motion may be a wide range of motion, including a fullbody motion to move the upper limbs and the lower limbs in coordination. These analyzing method and device are based on the assumption that the operating point matches the equilibrium point for the operating point in the static situation under the gravity compensation, and provide a user with a motion strategy (depending on the level of motion learning and the individual difference) that the central nervous system selects for a wide range of motion and such a motion status in an objective and quantitative manner under the clear standard, and provide them with specific means for motion-learning assistance. Various examples of the motion can be expected depending on the purpose, and the method and device can be applied to learning of motions and skills of various sports and acquisition of a motion and actions other than sports. That is, when the analyzing method and device are used for a method and a device of supporting the motion learning in order to establish an effective exercise or such intervention toward a target motion, feature amounts of the motion by a model person may be acquired beforehand, and a learner may be supported to learn the motion while referring to the feature amounts so as to bring their feature amounts to those of the model person. Alternatively, a learner may be supported to learn the motion while observing a change in their own feature amounts during each learning step.

The analyzing method and device as stated above may be used to a method and a device to evaluate the motion control for analysis of a motion-generation mechanism or a motion-learning mechanism of a healthy person and a brain-diseased patient, for example. In one form, motion skills may be diagnosed and evaluated based on the above-stated estimated two feature amounts in accordance with a motion command from a central nervous system, and motion learning may be promoted via additional feedback. Such a form is effective in the sports field and the rehabilitation field. In this way, the two feature amounts obtained from the present analyzing method can be effectively used for motion control evaluations and motion learning support.

The analyzing method and device may be used for an interface evaluation device to design and evaluate machines, tools and environment involving physical interactions with humans.

As described above, a motion analyzing device according to the present invention preferably includes: a myogenic potential detecting unit to detect a myogenic potential of a person who performs a motion; a motion detecting unit to detect a position of an endpoint of a limb of the person at a plurality of operating point positions; and a processor to calculate an equilibrium point of the person and a muscle synergy that is a set of base vectors describing the equilibrium point based on the myogenic potential detected by the myogenic potential detecting unit and the position of the endpoint of the limb detected by the motion detecting unit, the calculation being based on a musculoskeletal model of the person and a constraint condition that the position of the endpoint of the limb of the person matches the position of the equilibrium point in a static situation to keep a posture still under gravity compensation, wherein the processor includes: an AA muscle co-activation ratio calculating means to calculate an AA muscle co-activation ratio based on the detected myogenic potential; a muscle synergy calculating means to calculate a muscle synergy based on the position of the endpoint of the limb detected by the motion detecting unit and the AA muscle co-activation ratio calculated by the AA muscle co-activation ratio calculating means; and an equilibrium point calculating means to calculate the equilibrium point based on the AA muscle co-activation ratio calculated by the AA muscle co-activation ratio calculating means, the position of the endpoint of the limb detected by the motion detecting unit, and a muscle synergy calculated by the muscle synergy calculating means.

A motion analyzing method according to the present invention preferably includes: a myogenic potential detecting step of detecting a myogenic potential of a person who performs a motion; a motion detecting step of detecting a position of an endpoint of a limb of the person at a plurality of operating point positions; and a computing step of calculating an equilibrium point of the person and a muscle synergy that is a set of base vectors describing the equilibrium point based on the myogenic potential detected by the myogenic potential detecting step and the position of the endpoint of the limb detected by the motion detecting step, the calculation being based on a musculoskeletal model of the person and a constraint condition that the position of the endpoint of the limb of the person matches the position of the equilibrium point in a static situation to keep a posture still under gravity compensation, wherein the computing step includes: an AA muscle co-activation ratio calculating step of calculating an AA muscle co-activation ratio based on the detected myogenic potential; a muscle synergy calculating step of calculating a muscle synergy based on the position of the endpoint of the limb detected by the motion detecting step and the AA muscle co-activation ratio calculated by the AA muscle co-activation ratio calculating step; and an equilibrium point calculating step of calculating the equilibrium point based on the AA muscle co-activation ratio calculated by the AA muscle co-activation ratio calculating step, the position of the endpoint of the limb detected by the motion detecting step, and a muscle synergy calculated by the muscle synergy calculating step.

A motion analyzing program according to the present invention makes a motion analyzing device preferably function as: a measurement instruction means to instruct a myogenic potential detecting unit to detect a myogenic potential of a person who performs a motion and a motion detecting unit to detect a position of an endpoint of a limb of the person to detect a myogenic potential of the person and a position of the endpoint of the limb at a predetermined plurality of operating point positions; and a processor to calculate an equilibrium point of the person and a muscle synergy that is a set of base vectors describing the equilibrium point based on the myogenic potential detected by the myogenic potential detecting unit and the position of the endpoint of the limb detected by the motion detecting unit, the calculation being based on a musculoskeletal model of the person and a constraint condition that the position of the endpoint of the limb of the person matches the position of the equilibrium point in a static situation to keep a posture still under gravity compensation, wherein the processor includes: an AA muscle co-activation ratio calculating means to calculate an AA muscle co-activation ratio based on the detected myogenic potential; a muscle synergy calculating means to calculate a muscle synergy based on the position of the endpoint of the limb detected by the motion detecting unit and the AA muscle co-activation ratio calculated by the AA muscle co-activation ratio calculating means; and an equilibrium point calculating means to calculate the equilibrium point based on the AA muscle co-activation ratio calculated by the AA muscle co-activation ratio calculating means, the position of the endpoint of the limb detected by the motion detecting unit, and a muscle synergy calculated by the muscle synergy calculating means. The present invention may provide a recording medium having the motion analyzing program stored therein, and preferably a computer reads the motion analyzing program from the recording medium for execution.

These aspects of the invention eliminate the necessity of the MVC measurement in the conventional method to simplify the motion measurement and improve the analysis accuracy.

Preferably the myogenic potential detecting unit and the motion detecting unit detect a myogenic potential of the person and the position of the endpoint of the limb at a predetermined plurality of operating point positions. This configuration obtains feature amounts based on the measurement information at the plurality of positions and through statistic estimation, and so the accuracy to calculate the feature amounts improves.

Preferably the myogenic potential detecting unit and the motion detecting unit periodically detect a myogenic potential of the person and the position of the endpoint of the limb in the static situation, and the processor calculates an equilibrium point for every detection. This configuration obtains information on the variability of the equilibrium point at each of the limb endpoints. Such information can be effectively used for the diagnosis and treatment in rehabilitation and the assessment of the treatment, for example.

Preferably the myogenic potential detecting unit and the motion detecting unit periodically detect a myogenic potential of the person and the position of the endpoint of the limb during a motion by the person to move the position of the endpoint of the limb between one operating point position and another operating point position among the plurality of operating point positions, the AA muscle co-activation ratio calculating means calculates an AA muscle co-activation ratio based on the myogenic potential periodically detected during the motion, and the equilibrium point calculating means calculates an equilibrium point during the motion based on the muscle synergy calculated by the muscle synergy calculating means, the position of the endpoint of the limb and the AA muscle co-activation ratio obtained during the motion. This configuration obtains the equilibrium point during a motion to move the position of the limb endpoint of the person between the plurality of positions based on muscle synergies in the static situation at a predetermined plurality of positions and the AA muscle co-activation ratio obtained during the motion, and so the device is more versatile.

Preferably the limb of the person is an upper limb, and the antagonistic model of the muscles is a musculoskeletal system having three-paired six muscles that mimics an upper limb model from a shoulder to an elbow. This configuration enables numerical recognition of the status of a motion command from the central nervous system to implement the upper limb motion.

The above embodiments may be combined for implementation.

The above description is to be considered in all respects as illustrative and not restrictive. The technical scope of the present invention is defined by the claims, and is intended to include any modification within the meaning and scope equivalent to the terms of the claims.

REFERENCE SIGNS LIST

6 Camera
8 Electrode
10 Signal processor (measurement instructing unit)
20 Myogenic potential measuring unit (myogenic potential detecting unit)
30 Position measuring unit (motion detecting unit)
101 Myogenic potential measurement processor (myogenic potential detecting unit)
102 Position measurement processor (motion detecting unit)
103 AA muscle co-activation ratio calculating unit (processor)
104 Muscle synergy calculating unit (processor)
105 Equilibrium point calculating unit (processor)

The invention claimed is:

1. A motion analyzing device comprising:
a motion detecting unit to detect a position of a hand of a person who performs a motion, at a plurality of operating point positions;
a myogenic potential detecting unit to detect a myogenic potential of the person at the plurality of operating point positions; and
a processor to calculate a muscle synergy that is a base vector describing an equilibrium point that represents a position command from a central nervous system of the person when a position of the hand of the person is matched to the plurality of operating point positions, from the position of the hand, based on the myogenic potential detected by the myogenic potential detecting unit and the position of the hand detected by the motion detecting unit in a static situation to keep a posture still at the plurality of operating point positions of the hand of the person, wherein:
the processor includes an AA muscle co-activation ratio calculating unit; a muscle synergy calculating unit; and an equilibrium point calculating unit;
the AA muscle co-activation ratio calculating unit calculates an AA muscle co-activation ratio based on the myogenic potential detected by the myogenic potential detecting unit;
the equilibrium point calculating unit, by applying a constraint condition that an endpoint of the hand of the person at the plurality of operating point positions matches the equilibrium point in the static situation to keep a posture still under gravity compensation, calculates the endpoint of the hand of the person detected by the motion detecting unit as the equilibrium point; and
the muscle synergy calculating unit calculates the muscle synergy from the equilibrium point calculated by the equilibrium point calculating unit and the AA muscle co-activation ratio calculated by the AA muscle co-activation ratio calculating unit.

2. The motion analyzing device according to claim 1, wherein the myogenic potential detecting unit and the motion detecting unit synchronously detect the myogenic potential of the person and the position of the hand at a predetermined plurality of operating point positions.

3. The motion analyzing device according to claim 1, wherein the motion detecting unit detects the endpoint of the hand of the person and the myogenic potential detecting unit detects the myogenic potential of the person while keeping the hand of the person still at each of the plurality of operating positions.

4. The motion analyzing device according to claim 1, wherein the myogenic potential detecting unit detects the myogenic potential of the person while keeping the hand of the person still at each of the plurality of operating positions.

* * * * *